US005738721A

United States Patent [19]
Barron et al.

[11] Patent Number: 5,738,721
[45] Date of Patent: Apr. 14, 1998

[54] LIQUID PRECURSOR AND METHOD FOR FORMING A CUBIC-PHASE PASSIVATING/ BUFFER FILM

[75] Inventors: Andrew R. Barron, Cambridge; Michael B. Power; Andrew N. MacInnes, both of Quincy, all of Mass.

[73] Assignees: President and Fellows of Harvard College, Cambridge, Mass.; Triquint Semiconductor, Inc., Beaverton, Oreg.

[21] Appl. No.: 418,005

[22] Filed: Apr. 6, 1995

Related U.S. Application Data

[63] Continuation of Ser. No. 369,363, Jan. 6, 1995, abandoned.
[51] Int. Cl.$^6$ ............................................. C30B 25/02
[52] U.S. Cl. ............................................. 117/104; 117/954
[58] Field of Search ............................................. 117/104, 954; 556/70

[56] References Cited

U.S. PATENT DOCUMENTS

| | | | |
|---|---|---|---|
| 4,477,311 | 10/1984 | Mimura et al. | 156/643 |
| 4,839,145 | 6/1989 | Gale et al. | 422/245 |
| 4,952,527 | 8/1990 | Calawa et al. | 437/107 |
| 5,124,278 | 6/1992 | Bohling et al. | 117/104 |
| 5,168,077 | 12/1992 | Ashizawa et al. | 117/104 |
| 5,300,320 | 4/1994 | Barron et al. | 427/249 |
| 5,326,425 | 7/1994 | Gedridge et al. | 117/104 |
| 5,379,720 | 1/1995 | Kuramata | 117/104 |

OTHER PUBLICATIONS

Tabib-Azar et al., "Electronic Passivation of n-and p-type GaAs Using Chemical Vapor Deposited GaS," *Appl. Phys. Lett.*, 63 (5):625-267, (1993).

Cheng et al., "Submicrometer Self-Aligned Recessed Gate InGaAs MISFET Exhibiting Very High Transconductance," *IEEE Electron Device Letters*, 5(5):169-171, (1984).

Barnard et al., "Double Heterostructure $Ga_{0.47}In_{0.53}As$ MESFETs with Submicron Gates," *IEEE Electron Device Letters*, 9(9):174-176, (1980).

Fricke et al., A New GaAs Technology for Stable FET's at 300° C. *IEEE Electron Device Letters*, 10 (12) :577-579, (1989).

Carpenter et al., "Schottky Barrier Formation on $(NH_4)_2S$-Treated n-and p-type (100)GaAs," *Appl. Phys. Lett.*, 53(1):66-68, (1988).

Jenkins et al., "Gallium Arsenide Transistors: Realization Through a Molecularly Designed Insulator," *Science*, 263:1751-1753, (1994).

Nomura et al., "Preparation of $CuIn_5S_8$ Thin Films by Single–Source Organometallic Chemical Vapour Deposition," *Thin Solid Films*, 209:145-147, (1992).

Nomura et al., "Preparation and Characterization of n–and i–Butylindium Thiolate," *Polyhedron*, 8(6):763-767, (1989).

Sandroff et al., "Structure and Stability of Passivating Arsenic Sulfide Phases on GaAs Surfaces," *J. Vac. Sci. Technol. B*, 7(4) :841-844, (1989).

Wang et al., "Surface Passivation of GaAs with $P_2S_5$–Containing Solutions," *J. Appl. Phys.*, 71(6):2746-2756, (1992).

Turco et al., Thermal and Chemical Stability of Se–Passivated GaAs Surfaces, *J. Vac Sci. Technol. B*, 8(4):856-859, (1990).

Ueno et al., "Hetero–Epitaxy of Layered Compound Semiconductor GaSe Onto GaAs Surfaces for Very Effective Passivation of Nanometer Structures," *Surface Science*, 267:43-46, (1992).

Besser et al., "Comparison of Surface Properties of Sodium Sulfide and Ammonium Sulfide Passivation of GaAs," *J. Appl. Phys.*, 65(11):4306-4310, (1989).

(List continued on next page.)

*Primary Examiner*—Robert Kunemund
*Attorney, Agent, or Firm*—Hamilton, Brook, Smith & Reynolds, P.C.

[57] ABSTRACT

A chemical composition consists essentially $((t\text{-amyl})GaS)_4$. The chemical composition can be employed as a liquid precursor for metal organic chemical vapor deposition to thereby form a cubic-phase passivating/buffer film, such as gallium sulphide.

11 Claims, 1 Drawing Sheet

OTHER PUBLICATIONS

Tao et al., "S-Passivated Inp (100)–(1×1) Surface Prepared By a Wet Chemical Process," *Appl. Phys. Lett.*, 60(21): 2669–2671, (1992).

Nomura et al., "Single-Source Organometallic Chemical Vapour Deposition Process for Sulphide Thin Films: Introduction of a New Organometallic Precursor Bu"In(SPr$^i$)$_2$ and Preparation of In$_2$S$_3$ Thin Films," *Thin Solid Films*, 198:339–345, (1991).

Power et al., "Interaction of Tris-tert-butylgallium with Elemental Sulfur, Selenium, and Tellurium," *Organometallics*, 11 (3):1055–1063, (1992).

Power, M.B. and Barron, A.R., "Isolation of the First Gallium Hydrosulphido Complex and its Facile Conversion to a Ga$_4$S$_4$ Cubane: X-Ray Structures of [(Bu$^t$)$_2$Ga (μ-SH)]$_2$ and [(BU$^t$)GaS]$_4$", *J. Chem. Soc., Chem. Commun.*, 1315–1317, (1991).

Cowley, A.H., et al., "Tetrameric Gallium and Aluminum Chalcogenides, [tBuME]$_4$ (M = Al, Ga; E = S, Se, Te). A New Class of Heterocubanes", *Agew. Chem. Int. Ed. Engl.* 30(9):1143–1145 (1991).

MacInnes, A.N., et al., "Enhancement of photoluminescence intensity of GaAs with cubic GaS Chemical vapor deposited using a structurally designed single-source precursor", *Appl. Phys. Lett.* 62 (7) :711–713 (Feb. 1993).

Power et al., "New Cubane MOCUD Precusers for Gallium Sulfide . . . " Adv. Mates. Opt. Electron (1995) vol. 5(3) pp. 177–185.

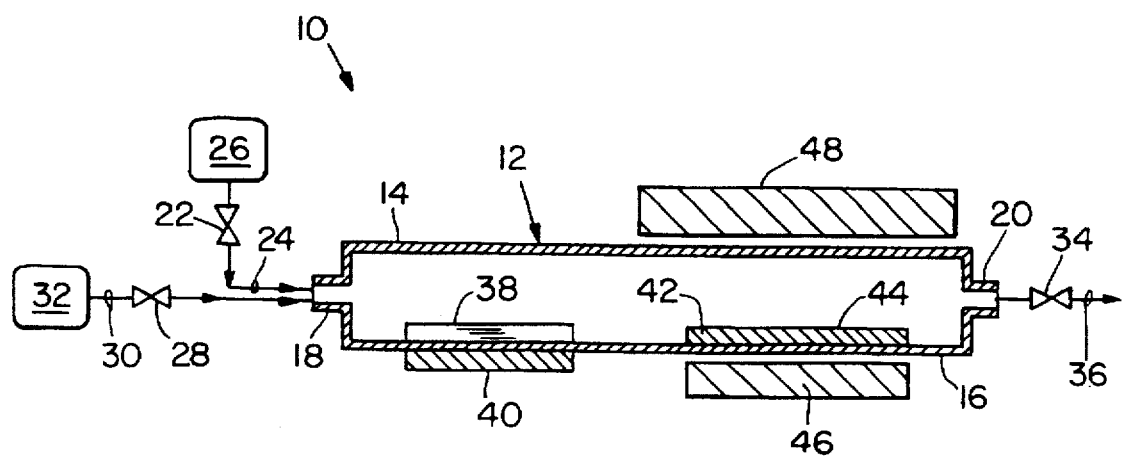

LIQUID PRECURSOR AND METHOD FOR FORMING A CUBIC-PHASE PASSIVATING/BUFFER FILM

RELATED APPLICATIONS

This is the continuation application of U.S. Ser. No. 08/369,363, filed Jan. 6, 1995 now abandoned.

GOVERNMENT FUNDING

This invention was sponsored by NSF Grant No. CHE-9222498 and ONR Contract Numbers N00014-91-J-1934 and N00014-94-I-0609 and the government has certain rights to the invention.

BACKGROUND OF THE INVENTION

Group 13–15 materials, and in particular, gallium arsenide (GaAs), have been employed recently in an increasing variety of electronic and electro-optical uses. For example, integrated circuits which are based on active layers of gallium arsenide, such as metal insulator semiconductor field-effect transistors (MISFETs), monolithic microwave integrated circuits (MMICs), and fast-logic circuits, have been employed in digital signal processing for military, biomedical, and communications systems applications. Gallium arsenide has also been employed in the fabrication of minority charge-carrier devices, such as solar cells and photodetectors. In addition, optical sources, such as lasers and light-emitting diodes (LEDs), have been developed which are of Group 13–15 materials, such as GaAs for the lasant medium.

However, surface states of gallium arsenide and related 13–15 semi-conductor materials provide sites for non-radiative recombination. Therefore, passivation is generally required to maintain the mobility of charge carriers. Examples of known methods of passivating gallium arsenide include deposition or growth of oxides, nitrides or sulfides by various techniques, such as molecular beam epitaxy (MBE), physical vapor deposition (PVD), or electrochemical deposition.

Alternatively, buffer layers are encapsulated to provide an intermediate transitional layer between a semiconductor substrate and subsequent layers to be formed over the substrate. For example, high-resistance buffer layers isolate circuits formed in active gallium arsenide layers from the underlying substrate. See, for example, U.S. Pat. No. 4,952,527, issued Aug. 28, 1990.

There are several problems associated with known methods of passivating gallium arsenide and with forming buffer layers on gallium arsenide. For example, more than one chemical precursor is typically required to form the chemical compound deposited on gallium arsenide substrate. Use of multiple precursors often causes formation of impurities and consequent irregular composition of the passivating/buffer layer by incorporation of impurities in the passivation layer during deposition. Further, some passivating/buffer layers, such as arsenic trisulfide, which can be formed by known methods, are often toxic. In addition, sulfurizing techniques generally form passivating layers which are relatively unstable. Also, known methods for deposition of passivating/buffer layers often require exposure of the gallium arsenide substrate to high temperatures, which can degrade the substrate. In addition, there are other problems commonly associated with known methods of deposition, such as slow deposition rates, and the requirement of expensive, complicated equipment for conducting deposition on gallium arsenide substrates.

Therefore, a need exists for an improved method for forming a passivating/buffer films on gallium arsenide or other semiconductor substrates, which overcome or minimize the above-listed problems.

SUMMARY OF THE INVENTION

The present invention relates to a liquid precursor for metal organic chemical vapor deposition onto substrates, and to chemical compounds which can be employed to form the liquid precursors. The present invention also relates to a method of forming a cubic-phase passivating/buffer film on a substrate which employs a liquid precursor.

The liquid precursor is a chemical composition consisting essentially of $((t\text{-amyl})GaS)_4$. Chemical compounds which can be employed to form the liquid precursor include $Ga(t\text{-amyl})_3$ and $((t\text{-amyl})_2Ga(SH))_2$.

The method of the invention includes heating a substrate to a temperature which causes a liquid precursor to volatilize and be deposited on the substrate. The liquid precursor, which consists essentially of a compound having the empirical formula of $((t\text{-amyl})GaS)_4$, is volatilized. A carrier gas is directed from a carrier gas source across the precursor source to conduct the volatilized precursor from the precursor source to the substrate, whereby the volatilized precursor is pyrolyzed and deposited on the substrate, thereby forming the cubic-phase passivating/buffer film on the substrate.

This invention has many advantages. For example, the film is formed by metal-organic chemical vapor deposition (MOCVD) from a single organometallic liquid precursor. Use of a liquid precursor enables a substantially constant flux of source vapors over a non-equilibrium percolation process, such as MOCVD. Further, the liquid precursor of the invention is essentially stable, both chemically and thermally, in the region bordered by evaporation and transport temperatures, even after prolonged use. The liquid precursor also decomposes to cause formation of a film having a substantially uniform crystal structure, resulting in a significantly reduced likelihood that defects will develop in the film. Further, cubic-phase films are formed, thereby enabling the formation of crystal structures which lattice match the structure of the substrate upon which additional films can be formed. In addition, the liquid precursor is easy to synthesize at a high level of purity. The liquid precursor is also oxidatively, hydrolytically, thermally and photochemically very stable under normal storage conditions.

BRIEF DESCRIPTION OF THE DRAWINGS

The Figure is a schematic representation of one embodiment of a system which is suitable for depositing a film on a substrate by the method of the invention.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principal features of the invention may be employed in various embodiments without departing from the scope of the invention.

The liquid precursor of the invention is a chemical composition that has the chemical formula of $((t\text{-amyl})GaS)_4$, and having an IUPAC name of tetrakis 1,1-dimethypropyl gallium sulfide).

The t-amyl component is a 1,1-dimethylpropyl group. Alternatively, indium can be employed instead of gallium, and selenium and tellurium can be employed instead of sulfur.

In one embodiment, the liquid precursor of the present invention is formed by conducting the following reaction steps:

$$GaCl_3 + 3(t\text{-amyl})MgCl \rightarrow Ga(t\text{-amyl})_3 + 3MgCl_2 \quad (1)$$

$$2Ga(t\text{-amyl})_3 + 2H_2S \rightarrow ((t\text{-amyl})_2Ga(SH))_2 + 2(t\text{-amyl})H \quad (2)$$

$$2((t\text{-amyl})_2Ga(SH)_2 \rightarrow ((t\text{-amyl})GaS)_4 + t\text{-amyl-H} \quad (3)$$

In one embodiment, where gallium and sulfur are employed, the resulting liquid precursor melts reversibly at 220°–221° C.

System 10, shown in FIG. 1, is one embodiment of a system which is suitable for conducting the method of the invention. System 10 includes housing 12 having first end 14 and second end 16. Inlet 18 is disposed at first end 14. Outlet 20 is disposed at second end 16. An example of a suitable housing is a laminar-flow hot-wall glass reactor. Alternatively, the system can include a suitable metal-organic vapor deposition reactor. An example of a suitable metal-organic vapor deposition reactor is disclosed in U.S. Pat. No. 4,839,145, the teachings of which are incorporated herein by reference. Valve 22 is disposed at conduit 24, which extends between carrier gas source 26 and inlet 18. Valve 28 is disposed at conduit 30, which extends between oxygen source 32 and inlet 18. Valve 34 is disposed at conduit 36, which extends from outlet 20.

Liquid precursor source 38 is disposed within first end 14 of housing 12. Precursor heating element 40 is disposed outside housing 12 at first end 14 and proximate to liquid precursor source 38. Precursor heating element 40 is suitable for heating liquid precursor at liquid precursor source 38 in an amount sufficient to volatilize the liquid precursor within first end 14 of housing 12.

Substrate 42, onto which a passivating/buffer film is to be formed by the method of the invention, is disposed within second end 16 of housing 12. Substrate 42 includes upward surface 44, which is suitable for deposition of a passivating/buffer film by the method of the invention. Substrate 42 within housing 12 is suitable for deposition of a passivating/buffer layer on upward surface 42 by the method of the invention. Examples of suitable semiconductor or electro-optical substrates include gallium, arsenide and indium phosphide substrates. A suitable metal, such as aluminum or a compound thereof, can be included in the crystal structure of substrate 42. A particular preferred substrate is gallium arsenide.

Heating plate 46 is disposed on the exterior of the housing 12 at second end 16 and is proximate to substrate 42. Heating plate 46 is suitable for heating substrate 42 within second end 16 of housing 12 in an amount sufficient to cause pyrolysis of volatilized precursor at second end 16 and consequent deposition of the pyrolyzed precursor onto upward surface 44 of substrate 42. Insulator 48 is disposed over housing 12 at second end 16.

When the desired amount of pyrolyzed precursor has accumulated on upward surface 44 of substrate 42, the flow of carrier gas from carrier gas source 26 into housing 12 is secured by closing valve 22. Also, precursor heating element 40 is allowed to cool, thereby discontinuing volatilization of precursor at precursor source 38. In addition, substrate heating plate 46 is allowed to cool, thereby allowing substrate 42 and the pyrolyzed precursor on substrate 42 to also cool.

In a particular preferred embodiment, the passivating/ buffer film formed on substrate 42 has an element in common with the crystal of substrate 42. For example, a passivating/buffer film of gallium sulfide, on a substrate of gallium arsenide, includes gallium as an element which is common to both the passivating/buffer film and substrate 42.

An insulating layer can be formed on the passivating/ buffer film disposed on substrate 42. Examples of suitable insulating layers include oxides, silicides, borides and carbides. In one embodiment, valve 28 is opened and an oxygen-containing gas is directed from oxygenation source 32 through conduit 30 and inlet 18 into housing 12. Examples of suitable oxygen-containing gases include oxygen gas ($O_2$), ditrogen oxide ($N_2O$) and ozone ($O_3$). The oxygen-containing gas is conducted to second end 16 of housing 12 and to substrate 42. Exposure of the passivating/ buffer film to the oxygen-containing gas causes a component of the passivating/buffer film at an exposed surface of the passivating/buffer film to oxidize, thereby forming an oxide layer on the passivating/buffer film.

The invention will now be further and specifically described by the following example. All parts and percentages are by weight unless otherwise specified.

EXAMPLE

Preparation of Tri-(tert-amyl)gallium

To $GaCl_3$(5.87 g, 0.03 mol) in 100 mL of pentane at room temperature under Argon with stirring was added 100 mL of 1.0M 1,1,-dimethylpropyl Grignard (tert-amyl Grignard, Aldrich). The addition took ca. 20 minutes, with the pentane solvent refluxing gently as the addition proceeded. As the third equivalent was being added, a white precipitate formed. The reaction vessel was covered with aluminum foil as the tri-tert-butylgallium analogue is known to be light sensitive, turning brown upon prolonged exposure to light. The mixture was stirred over the weekend. The thick white slurry mixture was then filtered through celite using a medium filter frit. The solvent was then removed from the filtrate under vacuum to leave a viscous brown/yellow liquid. Yield:65%. The $^1H$ and $^{13}C$ NMR spectra indicate essentially pure $GaR_3$ with no diethyl ether coordinated. NMR $^1H(C_6D_6)$1.54 (6H.q.J=7.54 Hz, $CH_2$), 1.18(18H, s,$CH_3$), 0.88(9H,t,J=7.5 Hz, $CH_3$). $^{13}C(C_6D_6)$ 39.07(s), 37.57(s), 28.55(s),14.55(s).

Preparation of ((Ctert-amyl)GaS)$_4$

The crude $R_3Ga$ from the previous preparation was dissolved in ca.30 mL of dry, distilled tolune under Argon and $H_2S$ was bubbled through the solution for ca.30 minutes, the mixture became slightly warm. In order to ensure that all the starting material had reacted $H_2S$ was then bubbled through the solution with warming of the solution gently with an air gun (ca. 60°–80° C.). The tolune solvent was then removed under vacuum to leave a gooey off-white solid. This was redissolved in pentane (10–15 mL) and set aside in the freezer overnight(−25° C.). This yielded (90%) a white crystalline material which proved by $^1H$ NMR to be ((t-amyl)$_2$GaSH)$_2$. Mp. 86°–90° C. NMR $^1H(C_6D_6)$ 1.55(8H, q.J=7.5 Hz, $CH_2$), 1.18(24H,s,$CH_3$), 0.95(12H,t,$CH_3$),0.82 (2H,s,$SH$). $^{13}C(C_6D_6)$36.41(s) , 32.16(s) , 28.16(s) , 11.35 (s).

The ((t-amyl)$_2$GaSH)$_2$compound was taken under argon and heated in the solid state with a hot air gun. The solid melted to give a clear liquid which upon continued heating, bubbled, giving off gas, and subsequently resolidified. Further continued heating (to ca. 230° C.), caused this new solid to melt. Upon cooling the melt resolidified. This was then dissolved in hexane (30 mL) and the clear solution set aside in the freezer overnight (−25° C.). This yielded (100%) a white crystalline material [t-amyl GaS]$_4$. Mp. 220°–221° C. NMR: $^1$H(C$_6$D$_6$) 1.55(2H,q,J=7.5 Hz, C$\underline{H}_2$), 1.16(6H,s, CH$_3$), 1.059(3H,t,J=7.5 Hz,C$\underline{H}_3$). $^{13}$C(C$_6$D$_6$) 35.62(s), 34.95 (s), 24.59(s), 12.16(s). Mass Spectrum (EI, m/e, %); 691 (M$^+$, 47%), 620(M$^+$—C$_5$H$_{11}$, 100%), 551(M$^+$—C$_5$H$_{11}$—C$_5$H$_9$, 30%), 478(M$^+$—3, t-amyl, 20%), 447, 408(M$^+$—4, t-amyl, 20%), 376.

The TGA indicated melting about 230° C. with subsequent loss of all the material up to about 300° C. under a flow of nitrogen at atmospheric pressure.

Stability studies on ((tert-amyl)GaS)$_4$

The above cubane was held at 240° C. (liquid state), under nitrogen, in three separate experiments for 8 hours, 24 hours and 72 hours respectively. NMR and mass spectroscopy of the cooled resolidified compounds indicated no change from the starting material.

Preparation of 3-methyl-3-chloropentane.

Following the general procedure for the preparation of tert-butyl chloride from tert-butyl alcohol and HCl (Organic Synthesis).

500 mL (4 moles) of 3-methyl-3 pentanol (Aldrich) and 1L of concentrated HCl (3 molar equivalent) were shaken together in a separatory funnel. The organic layer was then separated and washed with 1L of a 5% sodium bicarbonate solution, and then subsequently twice with one liter of water (to remove excess HCl). The organic layer was then set aside over anhydrous calcium chloride to dry. After drying for two hours the liquid was carefully decanted onto molecular sieves and left drying overnight. $^1$H NMR indicated pure product with no evidence of moisture. NMR; $^1$H(C$_6$D$_6$) 1.53 (4H, m, C$\underline{H}_2$CH$_3$), 1.27 (3H, s, CH$_3$), 0.85 (6H, t, CH$_2$C$\underline{H}_3$).

Preparation of 3,3-Diethylmethylmagnesium chloride

To 48.6 g of magnesium turnings (2 moles) under argon, in a 3-necked 2L flask equipped with a water condenser and a mechanical stirrer, containing 200 mL of diethyl ether was added 20–30 mg of iodine. 10 minutes later 25 mL of the chloride prepared above was added (neat) to the unstirred mixture. About 5 minutes later reaction was seen to begin (bubbles began to form). Stirring was then started (mechanical) and the reaction was seen to proceed with reflux of the ether solvent. The remaining chloride was added by dropping funnel at a rate sufficient to maintain gentle reflux of the ether solvent. The addition took ca. 3 hours. The mixture was then refluxed for an additional hour. The mixture (white precipitate) was then allowed to settle under argon overnight and was then filtered by cannula into a fresh flask and assayed in the normal way to yield a 0.93M solution.

Preparation of GaR$_3$(R=CEt$_2$Me)

To GaCl$_3$(26.41 g, 0.15 moles) in 1.5L of a 50:50 diethyl ether/pentane mixture (GaCl$_3$ dissolves exothermically), was added 500 mL of the 0.93M Grigand solution prepared above. The addition proceeded quickly and a large precipitate formed as the third equivalent was being added. After the addition was completed the mixture was refluxed for 2 hours and then left to settle without stirring. The mixture was then filtered through a medium frit to produce a lime-green filtrate. The solvent was then removed under vacuum to lease a viscous liquid. $^1$H NMR showed reasonably pure GaR$_3$. NMR; $^1$H(C$_6$D$_6$) 1.84 (6H, m, J=7.3 Hz, C$\underline{H}_2$CH$_3$), 1.50 (6H, m, J=7.3 Hz, C$\underline{H}_2$CH$_3$), 1.25 (9H, s, CC$\underline{H}_3$), 0.89 (18H, t, J=7.3 Hz C$\underline{H}_3$CH$_2$). $^{13}$C(C$_6$D$_6$) 45.03(s), 33.75(s), 24.22(s), 11.99(s).

Preparation of ((MeEt$_2$C)GaS)$_4$

To sulfur (3 g, 0.092 moles) in 50 mL of pentane under argon was added R$_3$Ga (R=C$_6$H$_{13}$, 10 g, 0.0307 moles) in 50 mL of pentane at room temperature via cannula. The yellow suspension was stirred overnight. The mixture was then filtered using a filter cannula. A sulfurous smell was noted. Some solvent was removed under vacuum and a white crystalline material was seen to form. The flask was put under argon and set aside in the freezer overnight (−25° C.), to yield some white crystalline material. This was filtered and dried under vacuum. The filtrate was removed of solvent under vacuum to yield unreacted GaR$_3$. Mp. 253°–255° C. NMR; $^1$H(C$_6$D$_6$) 1.68 (8H, m, J=7.2 Hz, C$\underline{H}_2$CH$_3$), 1.57 (8H, m, J=7.5 Hz, C$\underline{H}_2$CH$_3$), 1.18 (12H, s, CC$\underline{H}_3$), 1.05 (24H, t, J=7.5 Hz, CH$_2$C$\underline{H}_3$). 13C(C$_6$D$_6$) 41.32 (s, $\underline{C}$), 31.64 (s, $\underline{C}$H$_2$CH$_3$), 22.07 (s, CH$_3$), 11.24 (s, CH$_2$$\underline{C}$H$_3$). Mass Spectrum (EI, m/e, %); 748 (M$^+$, 40%), 663 (M$^+$—C$_6$H$_{13}$, 100%), 580 (M$^+$—C$_6$H$_{13}$—C$_6$H$_{11}$, 40%), 494 (M$^+$—3 C$_6$H$_{13}$, 20%). TGA is similar to the tert-amyl analogue except being approximately 30° C.

MOCVD of the Prepared Liquid Precursor

The chemical vapor deposition of GaS from the precursor [t-amyl GAS]$_4$ was performed on KBr, GaAs and Si substrates. Substrate pretreatments involved etching in HF/ethanol following a simple decreasing in soapy water before finally being immersed in aqueous ammonium sulfide. Substrates were then loaded wet (still covered in (NH$_4$)$_2$S) into the deposition chamber and heated to a temperature of ca. 400° C. and allowed to soak at this temperature for 2 hours. The precursor was then heated slowly to a final temperature of ca 250° C. to commence precursor sublimation and deposition.

At 200°C. the first signs of deposition were noted by visual examination. The appearance of color fringes on the wafers occurred as a result of light interference and indicated a deposited thickness of ca. 350° C. The precursor temperature was subsequently raised to 250° C. end-point and deposition continued for ca. 30 minutes.

Films were removed from the KBr wafers for transmission electron microscopic analysis. The as-removed films were found to be GaS in composition but were largely amorphous in nature. On annealing at 450° C. for 15 minutes the films exhibited a diffraction pattern consistent with a Zinc Blende cubic FCC phase. Hence, deposition at 400° C. presumably provided an amorphous deposition of the cubane molecular core that rearranged on annealing to give the Zinc Blende cubic structure.

Equivalents

Those skilled in the art will recognize, or be able to ascertain using no more than routine experimentation, many equivalents to the specific embodiments of the invention described specifically herein. Such equivalents are intended to be encompassed by the scope of the following claims.

We claim:

1. A cubane chemical of the composition of ((t-amyl) GaS)$_4$.

2. A method of forming a cubic-phase passivating/buffer film on a substrate, comprising the steps of:

a) heating the substrate to a temperature which causes a liquid precursor to volatilize and be deposited on the substrate;

b) volatilizing the liquid precursor, which consists essentially of a compound having the empirical formula of ((t-amyl)GaS)$_4$; and c) directing a carrier gas from a carrier gas source across the precursor source to conduct the volatilized precursor from the precursor source to the substrate, whereby the volatilized precursor is pyrolyzed and deposited on the substrate, thereby forming a cubic-phase passivating/buffer film on said substrate.

3. The method of claim 2, wherein the substrate includes potassium bromide.

4. The method of claim 2, wherein the substrate includes gallium arsenide.

5. The method of claim 2, wherein the substrate includes silicon.

6. A cubane chemical of the composition ((t-amyl)GaSe)$_4$.

7. A cubane chemical of the composition ((t-amyl)GaTe)$_4$.

8. A cubane chemical of the composition ((t-amyl)InS)$_4$.

9. A cubane chemical of the composition ((t-amyl)InSe)$_4$.

10. A cubane chemical of the composition ((t-amyl)InTe)$_4$.

11. A cubane chemical of the composition ((t-amyl)XY)$_4$ wherein X is a Group 13 material and Y is a chalcogenide material.

* * * * *